United States Patent [19]
Huston et al.

[11] 3,977,410
[45] Aug. 31, 1976

[54] DISPOSABLE FORCEPS

[75] Inventors: Paul O. Huston, Montville, N.J.;
John O. Freeborn, New Fairfield, Conn.

[73] Assignee: International Paper Company, New York, N.Y.

[22] Filed: Feb. 13, 1975

[21] Appl. No.: 549,695

[52] U.S. Cl. .................................. 128/354; 81/43
[51] Int. Cl.$^2$ .................. A61B 17/30; B25B 9/02
[58] Field of Search ....................... 81/43; 128/354

[56] References Cited
UNITED STATES PATENTS

| | | | |
|---|---|---|---|
| 1,610,925 | 12/1926 | Bryan .................................. | 128/354 |
| 2,685,880 | 8/1954 | Curutchet .......................... | 81/43 X |
| 3,140,715 | 7/1964 | Whitton, Jr. et al. ............ | 128/354 X |
| 3,367,336 | 2/1968 | Eizenberg ....................... | 128/354 X |
| 3,392,727 | 7/1968 | Hanlon ............................ | 128/354 X |
| 3,653,389 | 4/1972 | Shannon ........................... | 128/354 |

*Primary Examiner*—Channing L. Pace
*Attorney, Agent, or Firm*—Finnegan, Henderson, Farabow & Garrett

[57] ABSTRACT

A disposable forceps of a single piece of molded, resilient material is provided for surgical use. The forceps include a pair of arms substantially parallel to each other, integrally joined together at one end, and with the arms biased to an open position. At the other end of the arms are jaw members having teeth which precisely match and align together when the arms are urged to a closed position. Intermediate the ends of each arm is an integral alignment and spacing means projecting from the inner wall which interface and engage each other to allow movement of the arms in only one planar direction laterally to the open and closed positions and to limit the distance between the arms when the arms are biased to an open position, thereby ensuring proper alignment and matching of the jaw teeth.

8 Claims, 16 Drawing Figures

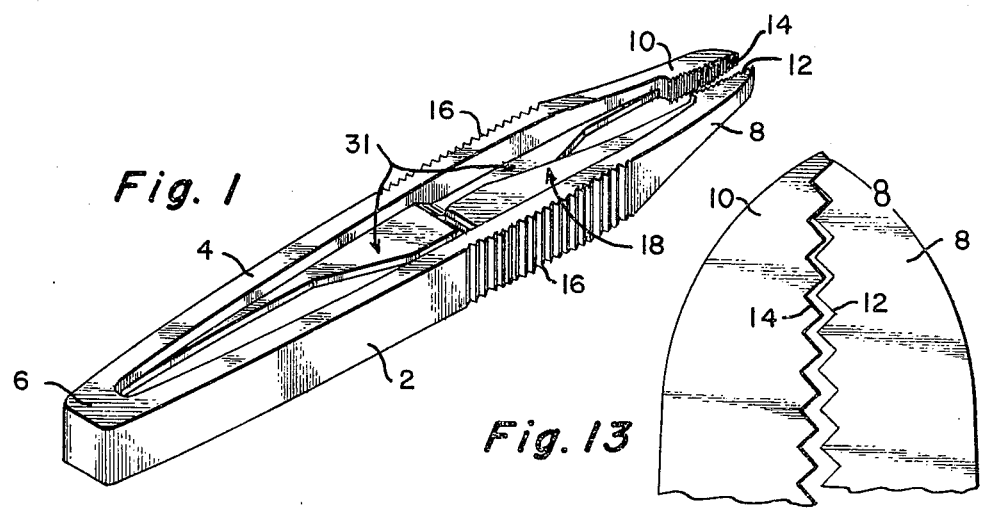
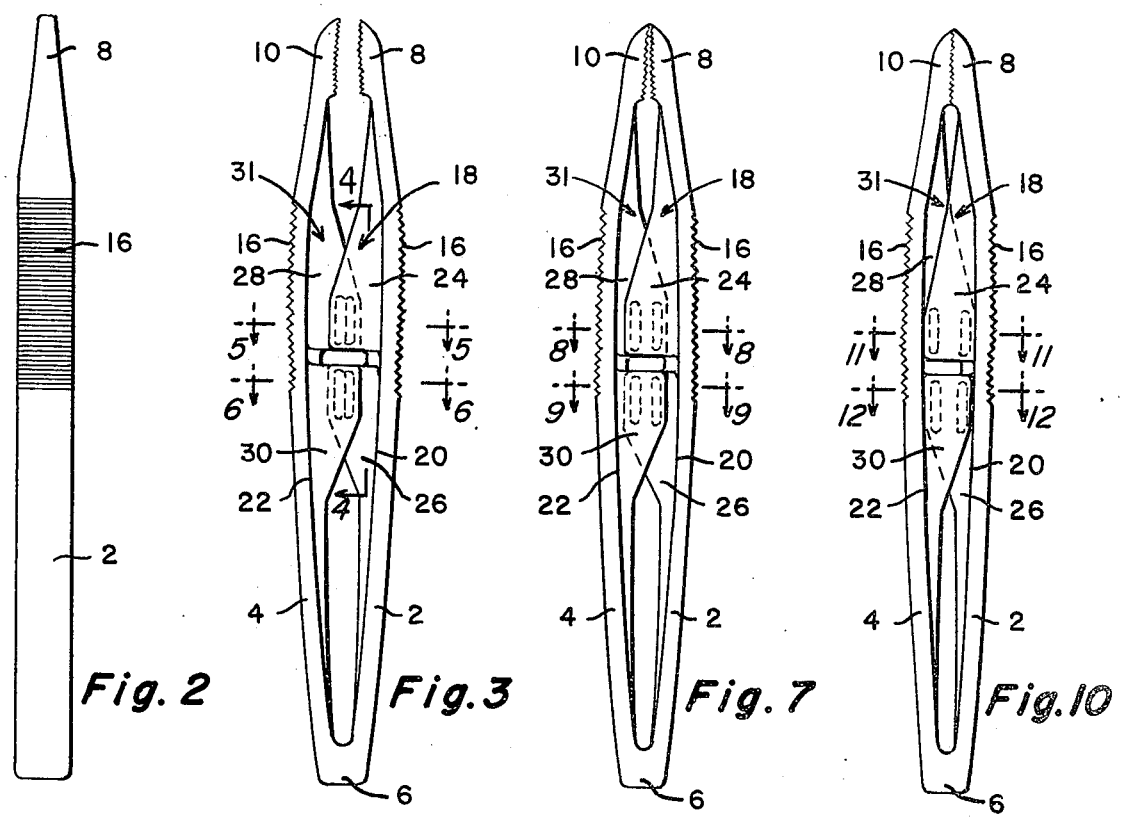
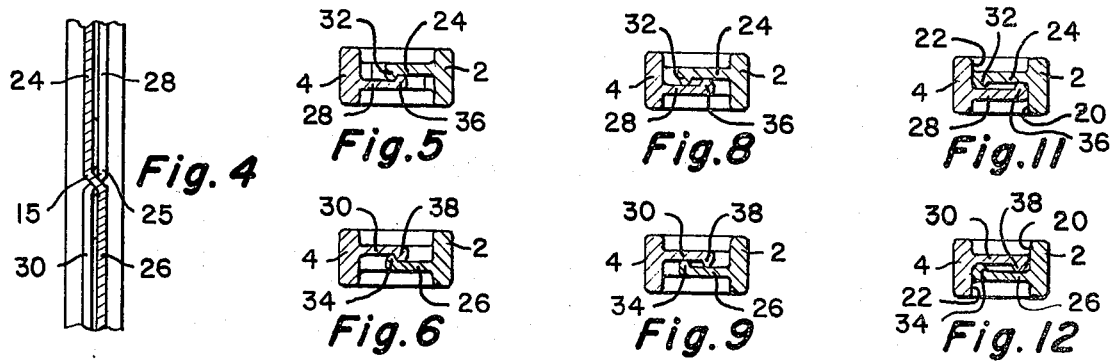

DISPOSABLE FORCEPS

The present invention relates to a disposable forceps used as a surgical instrument and, more particularly, to a disposable surgical forceps formed of a single piece of molded, resilient material.

In the prior art, diposable surgical instruments have been developed of single piece molded plastic construction. The prior art surgical instruments have, in general, been unsatisfactory because the instruments have been molded of plastic material that is easily bent to misalign the various components. This is unsatisfactory in surgical instruments requiring a fine alignment of teeth when in a closed position in order to obtain proper grasping.

Also disclosed in the art are tweezers having a type of guide member attached to the arms to accomodate a mating of the jaw teeth. Additionally, there are instruments disclosed having an element between the arms for adjusting the distance between the arms when in an inoperative or operative position. However, these tweezers either are not formed of a single piece of molded resilient material, do not include integral alignment means; or are not suitable for surgical purposes.

In view of the deficiencies of the prior art, it is an objective of this invention to provide in combination disposable forceps for surgical use that can be made of a single piece molded plastic construction which incorporates a resiliency required to bias the forceps in an open position, and, at the same time, provides integral alignment and spacing elements to allow movement of the arms in only one direction toward and away from each other and to limit the distance between the arms when the arms are biased to an open position.

It is another objective of this invention to provide easy grasping of the forceps and an alignment of the arms that is quick and that ensures a precise engagement and matching of the jaw teeth every time the forceps are closed.

Accordingly, the present invention provides a surgical forceps of single piece plastic construction which is compact in size, and easily and inexpensively manufactured thereby allowing it to be disposable, sufficiently resilient, and which has finely aligned jaw teeth.

Additional objectives and advantages of the invention will be set forth in part in the description which follows, and in part will be obvious from the description, or may be learned by practice of the invention. The objectives and advantages of the invention may be realized and attained by means of the instrumentalities and combinations particularly pointed out in the appended claims.

To achieve the foregoing objectives and in accordance with the purpose of the invention, as embodied and broadly described herein, this invention relates to a disposable forceps for surgical purposes that is molded of a single piece of resilient material. The disposable forceps comprises first and second substantially parallel arms integrally joined together at one end and having a spring-like resiliency in order to effect biasing the arms toward an open position; the other end of each arm having a jaw member; teeth on each jaw member, said teeth of one jaw member being precisely matched and aligned with the teeth of the other jaw member when the arms are urged to a closed position; and combined alignment and spacing means integrally formed intermediate the ends of each arm and projecting from the inner wall of each arm toward the other arm; said means interfacing and engaging each other to allow movement of the arms in only one planar direction laterally to the open and closed positions and limiting the maximum distance between the arms when the arms are positioned in an open position, thereby ensuring proper alignment and matching of said teeth.

Specifically, the integral alignment and spacing means includes a longitudinal web integrally formed intermediate the ends of each arm projecting from the inner wall of said arm toward the inner wall of the other arm, each longitudinal web having two integrally connected parallel sections of different planar levels, said sections of one web interfacing with corresponding sections of the other web in alternating levels to form a criss-cross mating relationship, and said sections having outer peripheral edges abutting the inner wall of the opposite arm when the arms are urged to a closed position; and a nodule on each section of each of said webs projecting inwardly toward the corresponding section of the other web, said nodules travelling along the opposite webs during operation of the forceps to allow movement of said arms in only one planar direction laterally to the open and closed positions thereby ensuring proper alignment and matching of said teeth, said nodules of one web engaging the opposing nodules of the other web when the arms are in the open position to limit the maximum distance between the arms.

It is also preferred that the forceps have finger grips located intermediate the ends of each arm on the outer wall of said arms to provide easy and firm grasping for operating the forceps.

The invention consists in the novel parts, constructions, arrangements, combinations and improvements shown and described. The accompanying drawings, which are incorporated in and constitute a part of this specification, illustrate one embodiment of the invention and, together with the description, serve to explain the principles of the invention.

OF THE DRAWINGS

FIG. 1 is a perspective view of the disposable forceps of a single piece of molded, resilient material constructed in accordance with the teachings of this invention;

FIG. 2 is a side view illustrating the disposable forceps of FIG. 1;

FIG. 3 is a top view of the forceps of FIG. 1 in a restricted but opened position;

FIG. 4 is a side section of the forceps taken along line 4—4 of FIG. 3 showing the sides of the arms, and the two connected sections of each alignment web;

FIG. 5 is a vertical section taken along line 5—5 of FIG. 3 showing the arms, the forward section of each alignment web, and the forward nodules when the forceps are in a restricted but opened position;

FIG. 6 is a vertical section taken along line 6—6 of FIG. 3 showing the arms, the rear section of each alignment web, and the rear nodules when the forceps are in a restricted but opened position.

FIG. 7 is a top view of the forceps of FIG. 1 in an intermediate position;

FIG. 8 is a vertical section taken along line 8—8 of FIG. 7 showing the arms, the forward section of each alignment web, and the forward nodules when the forceps are in an intermediate position;

FIG. 9 is a vertical section taken along line 9—9 of FIG. 7 showing the arms, the rear sections of each alignment web, and the rear nodules when the forceps are in an intermediate position;

FIG. 10 is a top view of the forceps of FIG. 1 in a closed position;

FIG. 11 is a vertical section taken along line 11—11 of FIG. 10 showing the arms, the forward sections of each alignment web, and the forward nodules when the forceps are in a closed position;

FIG. 12 is a vertical section taken along line 12—12 of FIG. 10 showing the arms, the rear section of each alignment web, and the rear nodules when the forceps are in a closed position;

FIG. 13 is a detailed top view of the jaw members of each arm when the forceps of FIG. 1 are in a semi-closed position.

Figure 14:
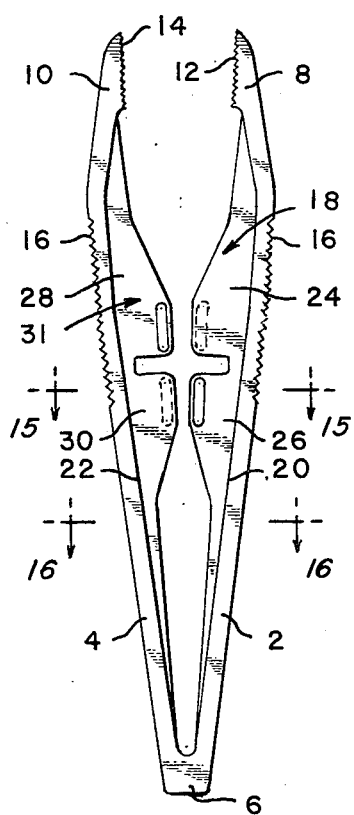
FIG. 14 is a top view of the forceps of FIG. 1 illustrated in its as-molded position.

Reference will now be made in detail to the present preferred embodiment of the invention, an example of which is illustrated in the accompanying drawings.

As shown in FIG. 1, the forceps comprise two substantially parallel arms 2 and 4 which are biased to an open position and integrally connected at one end at 6. At the other end of the arms are jaw members 8 and 10. Jaw member 10 has teeth 14 formed thereon which define a series of crowns and crevices respectively corresponding to and interlocking with a series of crevices and crowns defined by teeth 12 formed on jaw member 8 for precisely matching and aligning the teeth 12 and 14 of both jaw members together in an interlocking relationship when the forceps are forced to a closed position as shown in FIG. 13. On the outer surface of each arm and intermediate its ends is a roughened surface which serves as a finger grip 16, as shown in FIGS. 1 and 2.

Figure 16:
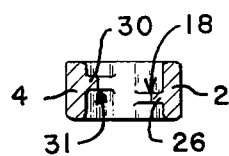
FIG. 16 is a sectional view of the forceps taken along line 16—16 of FIG. 14.

In accordance with the invention, the forceps are constructed of one piece of molded, resilient material such as any of the conventional thermoplastic or thermosetting resins and, preferably, one of the more rigid thermoplastic resins, for example, "Celcon" produced by Celanese Corporation. As shown in the figures illustrating the inoperative or non-grasping position and the operative or grasping position of the forceps, arm 2 has a longitudinal web 18 projecting from its inner wall 20 toward the inner wall 22 of the other arm 4. This web 18 has two integrally connected sections of different planar level sections 24 and 26 that interface with two corresponding planar level sections 28 and 30 of the longitudinal web 31 on arm 4 thereby forming a criss-cross mating relationship 15 and 25 as shown in FIG. 4. Sections 24 and 26 are formed with nodules 32 and 34 which slidingly contact the walls of the sections 28 and 30 while corresponding nodules 36 and 38 of sections 28 and 30 contact the walls of the sections 24 and 26 during the operation of the forceps. These nodules engage each other when the arms are biased in an open position. The purpose of this interfacing and engaging of webs and nodules is to allow movement of the arms 2 and 4 in only one planar direction laterally toward and away from each other, and to limit the distance between the arms 2 and 4 when the forceps are in the non-grasping position. Furthermore, the webs 18, 31 provide the arms 2, 4, respectively, with a T-shaped cross-section as can be seen in FIGS. 4, 5, and 16 which serves to strengthen the arms.

Figure 15:
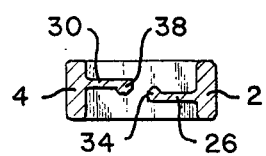
FIG. 15 is a sectional view of the forceps taken along line 15—15 of FIG. 14.

The arms 2 and 4 are biased toward an opened position due to the single-piece molded construction of resilient material. As is illustrated in FIGS. 14 and 15, the forceps are molded in a position where the arms 2, 4 are spaced apart a greater distance than the open position shown in FIG. 3 so that the webs 18, 31 are not overlapping or interfaced. To place in condition for use, the arms 2, 4 are forced together until the nodules 32 and 36 and nodules 34 and 38, respectively, snap over each other and the webs 18, 31 are interfaced. This greater spacing between the arms in the as-molded condition provides high inherent resiliency biasing the arms 2, 4 toward the open position. When in an open position, the arms 2 and 4 are limited to a predetermined distance between each other due to the size and placement of webs 18 and 31, and nodules 32, 34, 36, and 38. The nodules 32 and 34 of web 18 engage, respectively, nodules 36 and 38 of web 31 thereby preventing any further opening of arms 2 and 4. This is shown in FIGS. 5 and 6.

When the forceps are in an intermediate position, the arms 2 and 4 of respective webs 18 and 31 are being moved laterally to and from each other between the open and closed position. This is shown in FIGS. 7, 8, and 9. Referring to FIGS. 8 and 9, the nodules 32 and 34 of sections 24 and 26 of web 18 are travelling along the wall of sections 28 and 30 of web 31 while simultaneously nodules 36 and 38 of sections 28 and 30 of web 31 are travelling along the walls of sections 24 and 26 of web 18. In other words, when the forceps are being closed, the nodule 32 of the forward planar section 24 is intermediate its corresponding nodule 36 and arm 4 and moving towards arm 4 while nodule 36 is moving towards arm 2. Likewise, the corresponding nodule 34 on the rear planar section 26 is spaced from its corresponding nodule 38 and arm 4 and moving towards arm 4 while nodule 38 is moving towards arm 2.

When the forceps are in a closed position, the jaws 8 and 10 are in a grasping position with the respective series of crowns and crevices of the teeth 12 and 14 properly aligned and matched as shown in FIG. 13, and the arms 2 and 4, and webs 18 and 31 are positioned relative to each other as shown in FIGS. 10, 11, and 12. Referring to FIG. 11, the outer peripheral edge of planar section 24 of web 18 abuts the inner wall 22 of arm 4 while the outer peripheral edge of planar section 28 of web 31 abuts the inner wall of arm 2. Similarly, as shown in FIG. 12, the outer peripheral edge of planar section 26 of web 18 abuts the inner wall of arm 4 while the outer peripheral edge of planar section 30 of web 31 abuts the inner wall of arm 2. This abutment prevents any excessive force from being applied against the respective jaw members 8 and 10 and the sharp, finely matched teeth 12 and 14 and, therefore, prevents damaging the gripping teeth.

After the gripping force is released from the forceps at 16 when the forceps are in a closed position, the spring-like resiliency of the arms 2 and 4 inherently move the elements of the forceps through the intermediate position shown in FIGS. 7, 8, and 9 to the open position shown in FIGS. 3, 5, and 6. The open position, however, as previously mentioned, is limited to a predetermined distance by the engagement of nodules 32 and 36, and 34 and 38, respectively, shown in FIGS. 5 and 6. This predetermined distance is based upon the size and position of the webs and nodules.

It is contemplated that the jaw members may be molded to various widths, lengths, cross-sections or curvatures to suit different surgical purposes.

It can be seen that the forceps formed in accordance with this invention provide the desired accurate alignment of jaw teeth each time the forceps are closed, and due to this alignment and the limited movement of the forceps' arms, the fine gripping teeth are not subject to damage during use. Furthermore, the user need not exercise care in attempting to align the teeth because this is automatically accomplished. The forceps, being molded and of single-piece construction, are sufficiently inexpensive to permit them to be disposable. These forceps are particularly suitable for grasping sutures, since teeth of finer than normal construction can be used because of the guided movement of the arms.

What is claimed is:

1. Disposable forceps molded of a single piece of resilient material comprising:
   a. First and second arms integrally joined together at one end and molded into substantially parallel relationship for effecting an unfulcrumed springlike resiliency for biasing the arms toward an open position, and wherein each arm has at the other end a jaw member;
   b. teeth on each jaw member, wherein said teeth of one jaw member define a series of crowns and crevices respectively corresponding to and interlocking with a series of crevices and crowns defined by said teeth of the other jaw member for precisely matching and aligning the teeth of both jaw members together in an interlocking relationship when the arms are urged to a closed position; and
   c. combined alignment and spacing means integrally formed intermediate the ends of each arm and projecting from the inner wall of each arm toward the other arm, and having planar surfaces extending substantially along the length of each of said inner walls of said arms, and wherein said alignment and spacing means slidably interface and engage each other for allowing movement of the arms in only one planar direction laterally to the open and closed position and for limiting the maximum distance between the arms when the arms are biased to an open position, thereby ensuring proper alignment and matching of said teeth.

2. The disposable forceps of claim 1 including finger grips intermediate the ends of each arm on the outer wall of said arms to provide easy and firm grasping for operating the forceps.

3. Disposable forceps molded of a single piece of resilient material comprising:
   a. First and second substantially parallel arms integrally joined together at one end and having a spring-like resiliency in order to effect biasing the arms toward an open position, the other end of each arm having a jaw member;
   b. teeth on each jaw member, said teeth of one jaw member being precisely matched and aligned with the teeth of the other jaw member when the arms are urged to a closed position; and
   c. combined alignment and spacing means integrally formed intermediate the ends of each arm and projecting from the inner wall of each arm toward the other arm and comprising (i) a first longitudinal web projecting from the inner wall of the first arm toward the inner wall of the second arm, (ii) a second longitudinal web projecting from the inner wall of the second arm toward the inner wall of the first arm, said first and second webs interfacing and engaging each other, and each having an outer peripheral edge abutting the inner wall of the opposite arm when the arms are urged to a closed position, and wherein said first web includes at least one first nodule projecting inwardly toward the second web, and said second web includes at least one second nodule projecting inwardly toward the first web, said first nodule travelling along said second web and said second nodule travelling along said first web during operation of the forceps for allowing movement of said first and second arms in only one planar direction to the open and closed position, and said first nodule engaging said second nodule when the arms are in the open position for limiting the maximum distance between said first and second arms when the arms are biased to an open position, said alignment and spacing means thereby ensuring proper alignment and matching of said teeth.

4. Disposable forceps molded of a single piece of resilient material comprising:
   a. a pair of substantially parallel arms integrally joined together at one end and having a spring-like resiliency in order to effect biasing the arms toward an open position, the other end of each arm having a jaw member;
   b. teeth on each jaw member, said teeth of one jaw member being precisely matched and aligned with the teeth of the other jaw member when the arms are urged to a closed position; and
   c. a longitudinal web integrally formed intermediate the ends of each arm projecting from the inner wall of said arm toward the inner wall of the other arm, each longitudinal web having two integrally connected parallel sections of different planar levels, said sections of one web interfacing with corresponding sections of the other web in alternating levels to form a criss-cross mating relationship, and said sections having outer peripheral edges abutting the inner wall of the opposite arm when the arms are urged to a closed position, and a nodule on each section of each of said webs projecting inwardly toward the corresponding section of the other web, said nodules travelling along the opposite webs during operation of the forceps to allow movement of said arms in only one planar direction laterally to the open and closed positions thereby ensuring proper alignment and matching of said teeth, and said nodules of one web engaging the opposing nodules of the other web when the arms are in the open position to limit the maximum distance between the arms.

5. The disposable forceps of claim 4 including finger grips intermediate the ends of each arm on the outer wall of said arms to provide easy and firm grasping for operating the forceps.

6. Disposable forceps molded of a single piece of resilient material comprising:
   a. first and second substantially parallel arms integrally integrally joined together at one end and having a spring-like resiliency in order to effect biasing the arms toward an open position, the end of each arm having a jaw member;

b. teeth on each jaw member, said teeth of one jaw member being precisely matched and aligned with the teeth of the other jaw member when the arms are urged to a closed position; and c. first and second webs integrally formed intermediate the ends of each arm projecting from the inner wall of each arm toward the inner wall of the other arm, the first and second webs of each arm being in different parallel planes, the first web of the first arm interfacing with the first web of the second arm, the second web of the first arm interfacing with the second web of the second arm, at least one of said webs on each arm having outer peripheral edges abutting the inner wall of the opposite arm when the arms are urged to a closed position, and a nodule on each first web projecting inwardly toward the corresponding first web of the other arm, and travelling along the corresponding web during operation of the forceps to allow movement of said arms in only one planar direction laterally to the open and closed positions thereby ensuring proper alignment and matching of said teeth, and said nodule of the first web of the first arm engaging the nodule of the first web of the second arm when the arms are in the open position to limit the maximum distance between the arms.

7. The disposable forceps of claim 6 including finger grips intermediate the ends of each arm on the outer wall of said arms to provide easy and firm grasping for operating the forceps.

8. The disposable forceps of claim 6 wherein the first web of the first arm and the second web of the second arm are coplanar and where the second web of the first arm and the first web of the second arm are coplanar.

* * * * *

UNITED STATES PATENT OFFICE
CERTIFICATE OF CORRECTION

Patent No. 3,977,410   Dated August 31, 1976

Inventor(s) Paul O. Huston et al.

It is certified that error appears in the above-identified patent and that said Letters Patent are hereby corrected as shown below:

Claim 1, line 5, the word "springlike" should read --spring-like--.

Claim 6, line 4, the word "integrally", second occurrence, should be deleted being repetitive.

Signed and Sealed this

Seventh Day of December 1976

[SEAL]

Attest:

RUTH C. MASON
*Attesting Officer*

C. MARSHALL DANN
*Commissioner of Patents and Trademarks*